United States Patent [19]

Janese

[11] Patent Number: 4,817,587

[45] Date of Patent: Apr. 4, 1989

[54] RING PARA-SPINAL RETRACTOR

[76] Inventor: Woodrow W. Janese, 2806 N. Navarro, Suite M, Room B, Victoria, Tex. 77901

[21] Appl. No.: 91,811

[22] Filed: Aug. 31, 1987

[51] Int. Cl.$^4$ .............................................. A61B 17/02
[52] U.S. Cl. ...................................................... 128/20
[58] Field of Search .................................... 128/17–20

[56] References Cited

U.S. PATENT DOCUMENTS

| | | | |
|---|---|---|---|
| 1,839,726 | 1/1932 | Arnold | 128/20 |
| 1,919,120 | 7/1933 | O'Connor et al. | 128/20 |
| 2,586,488 | 2/1952 | Smith | 128/20 |
| 2,670,732 | 3/1954 | Nelson | 128/20 |
| 2,693,795 | 11/1954 | Grieshaber | 128/20 |
| 2,893,378 | 7/1959 | Cooper | 128/20 |
| 3,070,088 | 12/1962 | Brahos | 128/20 |
| 3,463,144 | 6/1966 | Hammond | 128/20 |
| 3,965,890 | 6/1976 | Gauthier | 128/20 |
| 3,998,217 | 12/1976 | Trumbull | 128/20 |
| 4,010,741 | 3/1977 | Gauthier | 128/20 |
| 4,099,521 | 7/1978 | Nestor et al. | 128/20 |
| 4,254,763 | 3/1981 | McCready et al. | 128/20 |
| 4,421,107 | 12/1983 | Estes et al. | 128/20 |

FOREIGN PATENT DOCUMENTS 12990  4/1928  Australia ............................... 128/20

Primary Examiner—Richard C. Pinkham
Assistant Examiner—Mark S. Graham
Attorney, Agent, or Firm—Paul L. DeVerter, II

[57] ABSTRACT

A para-spinal retractor for use during surgery which includes a planar ellipsoidal ring and a plurality of retractor blades which mount in the ring. The ring has a series of generally rectangular openings on either side of the major axis, and the blades have upturned rectangular cross-sections to slidably fit the openings. The blades are set in the tissue and rotated to a vertical position so that the ring openings engage the blades to maintain the retraction. The blades have angled facets and sharp tips, and are constructed so that when blades are engaged with the ring the facets project downwardly and towards the center of the ring.

7 Claims, 3 Drawing Sheets

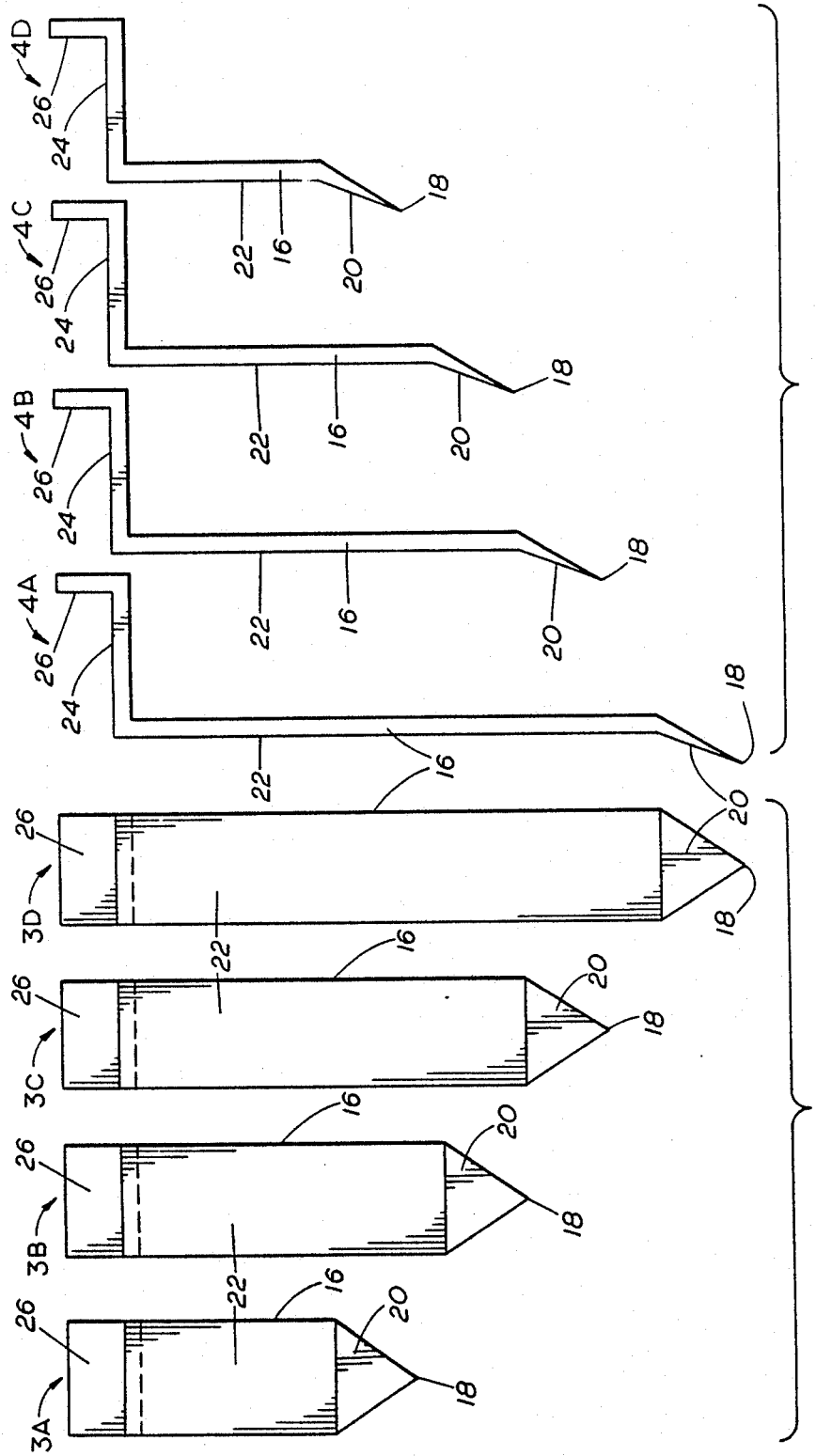

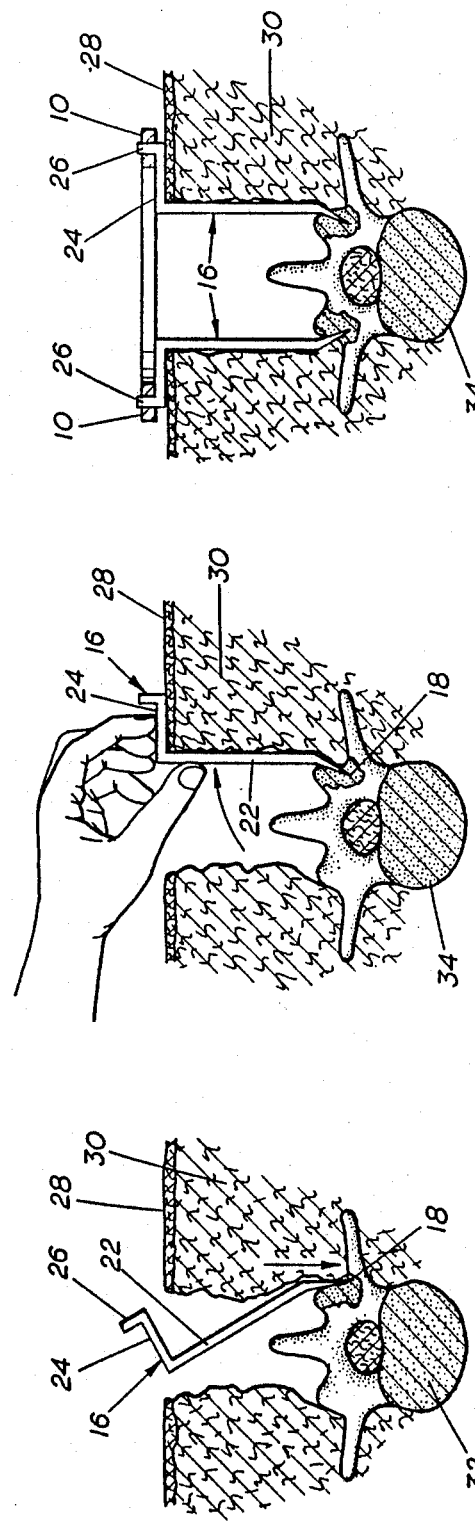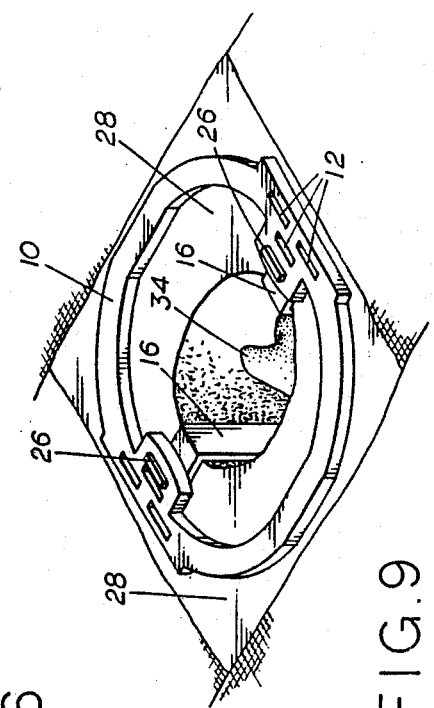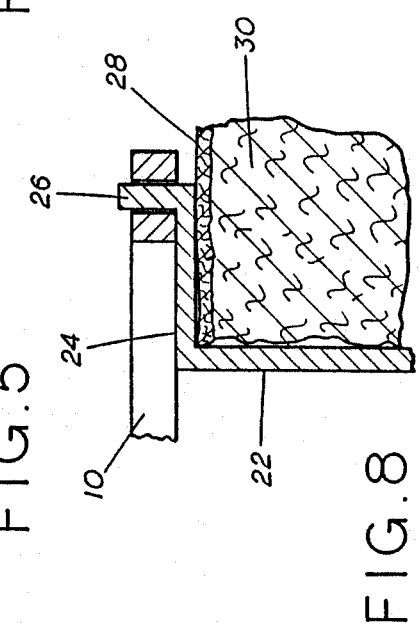

RING PARA-SPINAL RETRACTOR

The present invention relates generally to the field of surgical appliances, and more particularly to a retractor for use by a surgeon to hold back tissue lateral to the spinal column so as to provide better access to the region during a surgical operation.

BACKGROUND OF THE INVENTION

In the treatment of disease, it is necessary at times to operate on a diseased tissue to allow a patient to resume asymptomatic normal health. Numerous areas of the body are treated by surgery. Operations in the tissue of any depth requires a means to hold the incision open without injury to the retracted tissue while the surgeon operates upon the diseased or injured portion. This retraction decreases the required size of an incision, thereby aiding cosmesis, and allows improved visualization of pathology, while decreasing morbidity and mortality. Many apparatuses have been developed for surgical retraction, and a number of these have been the subject matter of U.S. patents. Examples of these are U.S. Pat. Nos. 3,070,088; 4,254,763; 2,893,378; and 3,965,890. These prior devices are designed for use when operating on various portions of the body, and involve a multiplicity of complex parts. They are not specifically designed for operating on the spine.

Retracting devices currently used in spinal surgery include the following: (1) self-retainer retractor with rack and pinion action, e.g., Valin Hemilaminectomy Retractor; (2) self-retaining retractor with ratchet action and hinged retractor arms, e.g., Scoville-Haverfield Hemilaminectomy Retractor; (3) self-retaining retractor with ratchet action, e.g., Scoville Hemilaminectomy Retractor, Glasser Laminectomy Retractor, Bagley Laminectomy Retractor; (4) self-retaining retractors, e.g., Meyerding Laminectomy Retractor, Popper-Gelpi Laminectomy Retractor, Knighton Hemilaminectomy Retractor; (5) self-retaining retractor with hinged arms, e.g., Beckman-Eaton Laminectomy Retractor, Cloward-Hoen Laminectomy Retractor, cone Laminectomy Retractor; and (6) hand-held retractor, e.g., Taylor Spinal Retractor, Myerding laminectomy Retractor.

The prior retractors are generally somewhat difficult to manipulate, difficult to install and maintain in the desired position, and are more complex than is necessary for their efficient utilization.

SUMMARY OF THE INVENTION

The present invention is particularly directed to a retractor for use when operating upon the spinal cord. More particularly, it is designed for lateral retraction of tissue from an incision along the spinal column.

The present invention consists of only two kinds of parts, namely a frame or ring, and a plurality of retractor blades, of varying heights, which are inserted into simple rectangular openings in the ring. Thus, the present invention is easily and efficiently manipulated, and requires a minimum of parts.

More particularly, the present retractor does not require counterweights nor does it require the use of an assistant for insertion and initial setting. The present invention provides a very low profile, thus reducing impediments to the surgeon. It has no moving parts, such as screws, bolts, or clamps which can loosen, and which increase the difficulty of sterilization. The design minimizes dislodgement and potential tissue injury, and requires neither new training for use, nor readjustment after implacement.

The length of the retractor blade to be selected is dependent upon the depth of the spine below the surface of the skin where the operation is to be performed. Other than the choice of this depth, no other adjustments need be made.

Thus, it is an object of the present invention to provide a ring para-spinal retractor which is relatively easy to manipulate, is stable, and has the features previously noted.

Other and further objects, features and advantages will be apparent from the following description of the presently preferred embodiment of the invention, given for the purpose of disclosure, when taken in conjunction with the accompanying drawings:

BRIEF DESCRIPTION OF THE DRAWINGS

Like character references designate like parts throughout the several views of the drawings, which are:

FIG. 3A-D is a front view showing various lengths of retractor blades;

FIG. 4A-D is a side view of the blades shown in FIG. 3;

FIG. 5 is a transverse view, partially in section, showing one of the retractor blades being inserted into a para-spinal muscle, adjacent to vertebrae;

FIG. 6 is a further view to FIG. 5, showing the retractor being rotated laterally to pull back the tissue;

FIG. 7 is a view, similar to FIG. 5, showing a second blade implaced opposite the first blade on the other side of the vertebrae, with the ring inserted to hold the blades in place;

FIG. 8 is a partial view, partially in section, showing the interconnection between the blade and the ring when in place, as in FIG. 7; and FIG. 9 is a partial perspective view showing the retractor in situ, demonstrating good operative exposure.

DESCRIPTION OF THE PREFERRED EMBODIMENT

Figure 2:
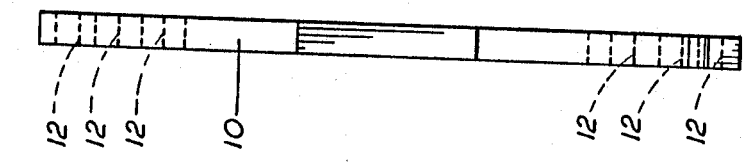
FIG. 2 is an end view of the ring.
Figure 1:
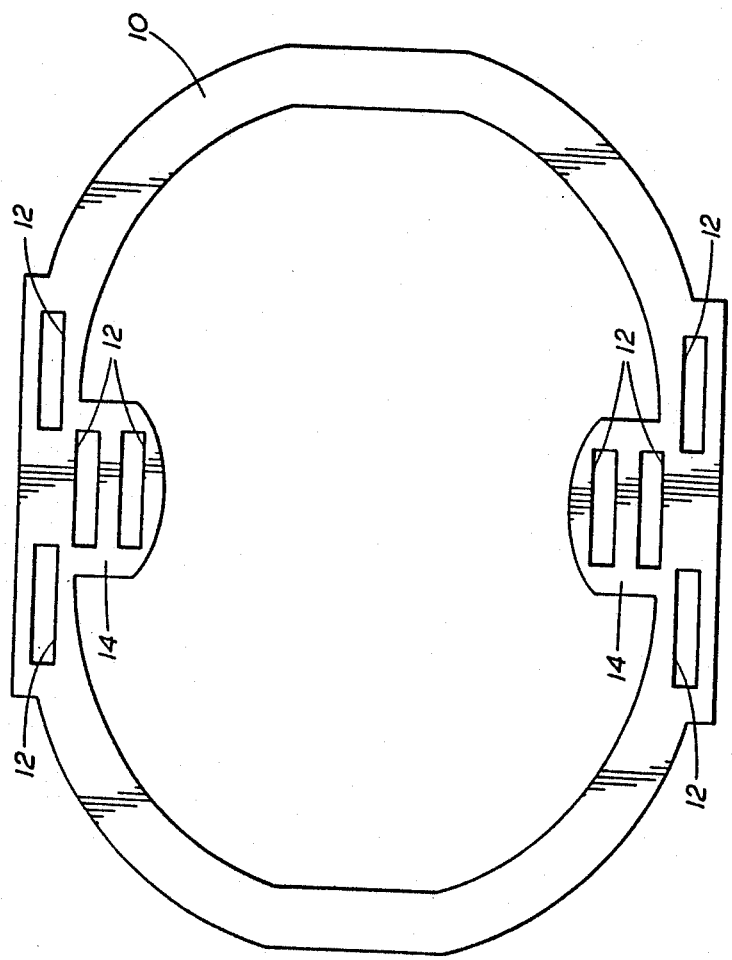
FIG. 1 is a plan view showing the generally oval frame or ring of the retractor, with the various rectangular openings therein.

Referring now to the drawings, and particularly to FIG. 1, the reference 10 refers to the frame or ring which forms a part of the present invention. The ring is generally oval or ellipsoidal in configuration, and as seen in FIG. 2, is plannar or flat. The cross-section of the ring 10 is shown as generally rectangular, although it may take other forms. Being oval in shape, the ring has both a major and minor axis. On the sides opposite the major axis are a series of generally rectangular openings or slots 12 placed symmetrically opposite each other. Extending inwardly along the minor axis of the ring is an extension 14 on either side. In each extension are additional openings or slots 12.

In the embodiment shown, the ring 10 cross-section is approximately 5 millimeters by 10 millimeters, and is made of AISI 316 stainless steel. The major and minor diameters of the ring may be 15 cm by 12 cm. A plurality of rectangular openings or slots 12 are set perpendicular to the plane of the ring 10, parallel to the major axis, and generally measure 3.5 millimeters by 20.5 millimeters.

Each extension 14 extends inwardly along the minor axis approximately 15 millimeters, leaving a clear area between the extensions of approximately 70 millimeters along the minor axis.

The blades, seen in FIGS. 3 and 4 are all essentially identical, varying only in their length. Each blade 16 generally comprises four portions. Each blade 16 has an impact point 18 located on a generally triangular facet 20. The facet is set at a downward angle of approximately 20° with respect to the length of the blade, and is arranged to point inwardly toward the center of the ring when in use. Each facet is approximately 15 millimeters long.

Above the facet 20 is the traction part 22 of the blade. The traction part, when in use, extends from the facet level 20 to the skin level. The length of the traction part 22 is varied, depending upon the depth of the operation, and it is utilized to hold the skin tissue laterally away from the incision.

As presently advised, it is believed that four lengths of traction parts 22 of the blades 16 are desirable. These lengths are 3.5, 5.5, 7, and 9.5 centimeters. It is further believed that a set of four blades of each length are desirable, although only 2, 3 or 4 blades of any particular length may be used at the same time.

Extending at right angles to the traction part 22 and away from the facet 20 is the skin surface part 24 of the blade 16. In use, the skin surface part would generally be horizontal (that is the same plane as the plane of the ring 10) and the underside of the skin surface part 24 would be adjacent and perhaps touching the skin of the patient being operated upon. The skin surface part 24 extends approximately 2.5 centimeters laterally from the traction part 22.

Finally, extending upwardly from the skin surface part 24, in a plane parallel with the traction part 22 is the ring coupling part 26. The ring coupling part 26 extends upwardly from the top of the skin surface part 24 approximately 1 centimeter. It is designed to be inserted into the opening or slot 12, and to be an easy slide fit therein. Consequently, if the opening 12 is made 20.5 millimeters by 3.5 millimeters, then the cross-section of the ring coupling part 26 would be made approximately ½ millimeter smaller, and thus would be 20 millimeters by 1.65 millimeters in cross-section dimensions. The object here is to allow an easy insertion, yet close fit, which will prevent turning and excess play.

It is presently preferred that the blades be manufactured of AISI type 316 stainless steel out of bars which are approximately 1.65 millimeters by 20 millimeters in cross-section. The impact points 18 are generally sharp and are designed to be inserted approximately 5 millimeters into the para-spinal muscles (multifidus, longissimus, and intertransversarius). Obviously, other lengths, angles, and slight modifications may become desirable as experience with the retractor of the present invention may show desirable.

In use, and referring now to FIGS. 5–9, and an incision is made through the skin 28 of the patient through the tissue 30 until the spinal column 32 is reached. Thereupon, and as seen in FIG. 5, the surgeon inserts the blade 16 through the incision, and then into the para-spinal muscle adjacent to the vertebrae 34 for a depth of approximately 5 millimeters. Care must be taken not to insert the point 18 deeper than 5 millimeters into the muscle, to avoid injury to the nerve root.

After the impact point has been secured, and referring now to FIG. 6, the blade 16 is rotated laterally against the tissue 30, with the point 18 acting as a fulcrum. This results in the traction part 22 retracting the tissue 30, and the skin surface part 24 may, depending upon the depth of the point 18, be adjacent to, or even touching the skin 28.

In a similar manner, a further blade 16 is inserted on the opposite side of the vertebra 34 and similarly rotated laterally. In the final position, the traction part 22 of each blade is parallel to that of the other blade, as seen in Figure 7. The surgical assistant then slips the ring 10 over the ring coupling part 26 of each inserted blade 16 and slides it down until the ring 10 contacts the upper side of the skin surface part 24. In this manner, the para-spinal tissue is held retracted laterally to improve the operative exposure, as is seen diagramatically in FIG. 9. Because the tissue 30 is elastic, it will be deformed with the lateral rotation of the blades 16, and will attempt to counter this rotation. However, the ring 10 prevents the movement of the tissue, so long as it is in place.

After the surgeon has finished the operation, the ring 10 is removed and the blades 16 are rotated and removed, where upon the incision may be closed, in accordance with normal medical practice. FIG. 8 illustrates, in somewhat greater detail, the interaction of the tissue 30, with the blade 16 and the ring 10, when the blade is implaced. FIG. 9 illustrates the accessibility of the vertebrae to the surgeon using the retractor of the present invention. Depending upon the placement and procedure to be initiated, two or more blades 16 may prove desirable.

Thus, it is seen that the para-spinal retractor of the present invention provides a unique retractor particularly useful for lateral retraction in spinal operations. The present invention, therefore, is well adapted to carry out the objects and attain the ends and advantages mentioned, as well as other inherent therein. While a presently preferred embodiment has been given for the purpose of disclosure, numerous changes in the details of construction, and the combination, shape, size and arrangement of the parts and uses may be restored to without departing from the spirit and scope of the invention.

What is claimed is:

1. A para-spinal retractor, for retracting and holding apart tissue adjacent the spinal column during surgery including:
   a generally planar ellipsoidal ring,
   at least two generally rectangular openings transverse to the plane of the ring, the openings being parallel to, and located symmetrically on either side of, the major axis of the ring,
   at least two elongate retractor blades which include tissue retracting surfaces, and
   each blade including a rectangular upstanding ring coupling part means arranged to slidably fit within the rectangular opening of the ring, (whereby the tissue is held retracted by the blades when the ring is inserted over the ring coupling parts.)
   a skin surface part, set perpendicular to the ring coupling part means, and arranged to be adjacent the skin surface of the tissue,
   a traction skin, set perpendicular to the skin surface part and spaced toward the major axis of the ring when the blade is inserted in the ring, and arranged to retract tissue, and a facet portion, set at an angle downwardly from the skin surface part and towards the interior of the ring when the blade is inserted in the ring, whereby the tissue is held retracted by the blades when the facet is inserted in the tissue of the spinal column and the ring is inserted over the ring coupling part means and adjacent the skin surface part.

2. The invention of claim 1 wherein the length of the traction part is between 3.5 and 9.5 centimeters in length.

3. The invention of claim 1 including an extension on the inside of each side of ring, at the minor axis, each extension having at least one additional rectangular opening therethrough.

4. The invention of claim 1 wherein the end of the facet portion of the blade is sharp.

5. In a para-spinal retractor (of the type), for retracting and holding apart tissue adjacent the spinal column during surgery, including a generally flat elliposoidal ring and a plurality of elongate retractor blades attachable to the ring, the improvement comprising:

each blade having a traction part arranged to be inserted into and rotated to a vertical position in an incision adjacent the spine, a facet portion extending downwardly from and at an angle towards the interior of the ring from the traction part, and arranged for insertion in the tissue of the spinal column prior to rotation of the blade, a skin surface part of the blade extending perpendicular to the traction part and away from the incision, a ring coupling part of the blade, extending upwardly perpendicular to the skin surface part, and having a generally rectangular cross-section, and the ring having a plurality of rectangular openings, arranged perpendicular to the ring, and sized to closely, yet slidably, engage the ring coupling part and rest on the skin surface part of the blade, when the traction part of the blade is vertical.

6. The invention of claim 5 wherein the rectangular openings are parallel to the major axis of the ring.

7. The invention of claim 6 including an extension on the inside of each ring, at the minor axis, each extension having at least one additional rectangular opening therethrough parallel to the major axis of the ring.

* * * * *